United States Patent [19] [11] 4,210,636
Lien et al. [45] Jul. 1, 1980

[54] ANTISECRETORY POLYPEPTIDES

[75] Inventors: Eric L. Lien, Paoli; Dimitrios Sarantakis, West Chester; Norman H. Grant, Wynnewood, all of Pa.

[73] Assignee: American Home Products Corporation, New York, N.Y.

[21] Appl. No.: 906,813

[22] Filed: May 17, 1978

[51] Int. Cl.$^2$ .................... A61K 37/02; C07C 103/52
[52] U.S. Cl. ............................. 424/177; 260/112.5 S
[58] Field of Search ................. 260/112.5 S; 424/177

[56] References Cited
PUBLICATIONS

J. Rivier et al., Biochem. and Biophys. Res. Comm. 65, (1975), pp. 746–750.
J. Rivier et al., "Peptides", 1976, pp. 439 & 440.

Primary Examiner—Delbert R. Phillips
Attorney, Agent, or Firm—Richard K. Jackson

[57] ABSTRACT

Three polypeptides of the formulae [des-Ala$^1$-Gly$^2$], Ala$^5$, Ser$^6$-SRIF, Met$^7$-SRIF and [des-Ala$^1$-Gly$^2$-Lys$^4$], (3-mercapto-1-oxopropyl)$^3$-SRIF possessing gastric anti-secretory activity are useful anti-ulcer agents.

6 Claims, No Drawings

ANTISECRETORY POLYPEPTIDES

BACKGROUND OF THE INVENTION

Somatostatin and certain analogues of somatostatin have been observed inhibit gastric acid secretion. U.S. Pat. No. 4,061,626 discloses the activity of somatostatin, D-Lys$^4$-SRIF and D-Ala$^2$, D-Lys$^4$-SRIF as gastric acid secretion inhibitors as well as inhibitors of growth hormone, glucagon and insulin secretion. U.S. Pat. No. 4,062,816 discloses the activity of D-Ala$^5$-SRIF as an inhibitor of gastric acid secretion as well as an inhibitor of growth hormone secretion. Lippmann et al., Pharmac. Res. Comm., 8, 445 (1976) discloses gastric acid secretion inhibition by somatostatin and several analogues, noting that D-Lys$^9$-SRIF had no appreciable effect on gastric acid secretion at a dose as high as 2 μm/Kg, s.c.

DESCRIPTION OF THE INVENTION

In accordance with this invention there is provided a group of novel polypeptidic anti-ulcer agents, pharmaceutical compositions containing the anti-ulcer agents and methods for their use.

The anti-ulcer agents of this invention function as anti-secretory agents to reduce (1) total gastric volume, (2) hydrogen ion secretion, or (3) hydrogen ion concentration. The reduction in any one of these parameters aids in attenuating the general debilitating influence of a peptic ulcer. The use of compounds exhibiting anti-secretory activity in the curative and/or prophylactic treatment of peptic ulcer disease is an established, beneficial procedure.

The anti-secretory agents of this invention are polypeptide analogues of somatostatin of the formulae:

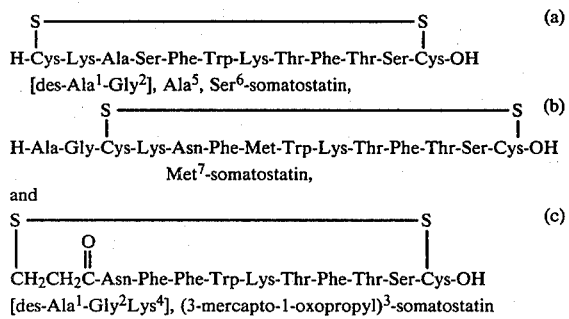

and the reduced linear form of those compounds in which two mercapto groups appear as the precursors of the depicted disulfide cycle.

Non-toxic, pharmaceutically acceptable salts of the reduced linear and cyclic polypeptides are produced by methods known to the art from such organic and inorganic acids are hydrochloric, hydrobromic, sulfuric, phosphoric, polyphosphoric, maleic, acetic, citric, benzoic, succinic, malonic, ascorbic. Acetic acid salts are most commonly employed and to that extent are preferred.

Each of the polypeptides of this invention was tested and found active parenterally (s.c.) in the scientifically recognized, standard test for anti-secretory activity which involves the following procedure in which male Charles River rats weighing 190–260 grams are deprived of food but not water for eighteen hours prior to use. Water is withheld during the actual experiment. The rats are weighed, anesthetized with ether and the pylorus is ligated according to the method of Shay et al., Gastroenterology, 26, 906–913 (1954). Treatment or vehicle control is then administered subcutaneously (s.c.). The rats are housed two per cage and sacrificed with $CO_2$ four hours after ligation. The stomachs are removed, rinsed, and contents emptied into a graduated centrifuge tube. The tubes are centrifuged for twenty minutes at two thousand revolutions per minute and the volume of gastric juice is recorded. Any sample which is obviously contaminated with feces, food or blood is eliminated. An aliquot of each sample is frozen for later analysis of pepsin. The pH is measured and one milliliter of gastric juice is titrated with 0.1 N NaOH to a pH of 7.0–7.4. The data are analyzed by analysis of variance and, using the pooled error variance, t-comparisons are made between the groups.

Thus, the anti-secretory agents of this invention are for use in treating peptic ulcer disease by administering them, parenterally to a mammal in need thereof in an amount sufficient to alleviate the debilitating effects of said disease. The polypeptides may be administered neat or as a composition. Suitable liquid compositions include sterile solutions for parenteral administration. The polypeptides may be employed alone as the sole basis for treatment or they may be advantageously employed in conjunction with a treatment regimen utilizing a conventional antacid such as calcium carbonate, magnesium carbonate, bismuth carbonate, aluminum or magnesium hydrated oxides, magnesium glycinate, magnesium trisilicate, calcium trisilicate, or sodium bicarbonate to maintain gastric acidity from about a pH of 3 to 5 or higher. Likewise, the anti-secretory agents of this invention may be used in conjunction with known anticholinergic agents or known $H_2$-receptor blocking agents.

The pharmaceutical compositions containing the antisecretory agents of this invention are formulated conventionally with a sterile liquid carrier. Unit dosage forms containing from about 1 to 50 milligrams of polypeptide are especially suitable.

As with any gastric ulcer disease treatment, the dosage and treatment regimen employing an anti-secretory agent is entirely subjective and must be regulated by the physician to the individual patients need subject to such variables as age, severity of the condition, mode of administration, companion medication, response to the treatment, etc. Therefore, the dose of polypeptide to be employed in any given case must be determined by the attending physician.

Although the compounds of this invention are analogues of somatostatin, they demonstrate no meaningful reduction in growth hormone, insulin or glucagon when tested in vivo by standard methods. Hence, they afford effective means for combatting peptic ulcer disease where no concomitant reduction in secretion of growth hormone, insulin and glucagon is desired.

The anti-secretory polypeptides of this invention are produced by conventional procedures in the polypeptide art. The specific examples, infra, illustrate the solid phase technique of synthesis. The classical methods of synthesis are similarly applicable to the synthesis of the compounds herein disclosed.

The potency of each compound is reported at the end of each example illustrating its production. The potency reported is the lowest dose administered at which two of the three parameters (a) total gastric volume, (b) hydrogen ion secretion, and (c) hydrogen ion concentration, were significantly decreased. In addition, the maximum dose employed to evaluate control of growth hormone, insulin and glucagon secretion is reported. Somatostatin effectively inhibits secretion of growth hormone, insulin and glucagon in that test procedures at about 10 micrograms per kilogram.

EXAMPLE I tert-Butyloxycarbonyl-S-p-methoxybenzyl-L-cysteinyl-ε-2-chlorobenzyloxycarbonyl-L-lysyl-L-alanyl-O-benzyl-L-seryl-L-phenylalanyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxymethyl-polystyrene ester.

tert-Butyloxycarbonyl-S-p-methoxybenzyl-L-cysteine hydroxymethyl polystyrene was treated according to schedule A for the incorporation of, Boc-Thr(Bzl)-Ser(Bzl)—OH, Boc-Thr(Bzl)-Phe—OH, Boc-Lys(ClZ)—OH, Boc-Trp—OH, Boc-Phe—OH, Boc-Ser(Bzl)—OH, Boc-Ala—OH, Boc-Lys(ClZ)—OH, and Boc-Cys(SMBzl)—OH to afford the title peptidoresin.

Schedule A
1. Wash with $CH_2Cl_2 \times 3$.
2. Treat with TFA-$CH_2Cl_2$-EDT (1:1:5%, v/v) for 5 min.
3. Treat as in 2 for 25 minutes
4. Wash with $CH_2Cl_2 \times 3$.
5. Wash with DMF.
6. Treat with 12% TEA in DMF twice for 3 minutes.
7. Wash with DMF.
8. Wash with $CH_2Cl_2 \times 3$.
9. Treat with 4 equivalents of the corresponding amino acid derivative in $CH_2Cl_2$-DMF and stir for 5 min.
10. Add in two portions 5 equivalents of DIC dissolved in $CH_2Cl_2$ and over a period of 30 min. Reaction time 6 hours.
11. Wash with DMF $\times 3$.
12. Wash with $CH_2Cl_2 \times 3$.
13. Test ninhydrin reaction according to Kaiser et al., Annal. Biochem. 34, 595 (1970). In case of incomplete reaction repeat lines 9 to 13 above.

EXAMPLE II

S-p-methoxybenzyl-p-mercaptopropionyl-L-asparaginyl-L-phenylalanyl-L-phenylalanyl-L-tryptophyl-ε-2-chlorobenzyloxycarbonyl-L-lysyl-O-benzyl-L-threonyl-L-phenyl-alanyl-O-benzyl-L-threonyl-O-benzyl-L-seryl-S-p-methoxybenzyl-L-cysteinyl-hydroxymethyl polystyrene ester.

Boc-Cys(SMBzl)-O-Resin was treated as in example I for the incorporation of Boc-Thr(Bzl)-Ser(Bzl)-OH, Boc-Phe-OH, Boc-Thr(Bzl)-OH, Boc-Lys(ClZ)-OH, Boc-Trp-OH, Boc-Phe-OH, Boc-Phe-OH, Boc-Asn-OH, and S-p-methoxybenzyl-β-mercaptopropionic acid (MPA) to afford the title peptidoresin.

EXAMPLE III tert-Butyloxycarbonyl-L-alanyl-glycyl-S-p-methoxybenzyl-L-cysteinyl-ε-2-chlorobenzyloxycarbonyl-L-lysyl-L-asparaginyl-L-phenylalanyl-L-methionyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl hydroxymethyl polystyrene ester Boc-Cys(SMBzl)-O-Resin was treated as in example I for the incorporation of Boc-Ser(Bzl)—OH, Boc-Thr(Bzl)—OH, Boc-Phe—OH, Boc-Thr(Bzl)—OH, Boc-Lys(ClZ)—OH, Boc-Trp-OH, Boc-Met—OH, Boc-Phe-OH, Boc-Asn—OH, Boc-Lys(ClZ)-OH, Boc-Cys(SMBzl)—OH and Boc-Ala-Gly—OH.

EXAMPLE IV

L-Cysteinyl-L-lysyl-L alanyl-L-seryl-L-phenylalanyl-L-tryptophyl-L-lysyl-L-threonyl-L-phenylalanyl-L-threonyl-L-seryl-L-cysteine cyclic (1→12) disulfide The peptido resin of example I (18 g.) was mixed with anisole (20 ml.) and treated with liquid HF for 45 minutes in an ice-bath. The excess HF was removed as fast as possible under vacuo and the residue was extracted with 2 M aq. AcOH. The solution was diluted with water to 2.5 liters and the pH was brought to 7.5 with dil. $NH_4OH$. The mixture was left to stand for 48 hours, acidified to pH 5 with gl. acOH and lyophilized. The crude material was chromatographed through a column of Sephadex G-25 (2.5×150 cm) and the material which emerged on elution with 1 M-aq. AcOH in tubes 126 to 196 (110 drops each fraction) was pooled and lyophilized. This material was chromatographed again through Sephadex G-25 (2.5×150 cm.) and eluted with 0.5 M-aq. AcOH, to afford the title compound, 427 mg. $R_f$(BWA, 4:1:1) 0.45, $R_f$(BWAP, 30:6:24:20) 0.73 Amino acid analysis: Thr (2) 2.07, Ser (2) 1.77, Ala (1) 0.99, Cys (2) 1.37, Phe (2) 1.99, Lys (2) 2.01, Trp. N.D. Antisecretory Potency: at 26.3 mg/kg, total gastric volume and hydrogen ion secretion were significantly reduced.

Growth hormone, insulin and glucagon secretion were not inhibited at 3.10 mg/kg, the highest dose tested.

EXAMPLE V

β-Mercaptopropionyl-L-asparaginyl-L-phenylalanyl-L-phenylalanyl-L-tryptophyl-L-lysyl-L-threonyl-L-phenylalanyl-L-threonyl-L-seryl-L-cysteine cyclic (1→11) disulfide The peptidoresin of example II (10 g.) was deprotected and oxidized to the cyclic disulfide form as described in example IV to afford crude material (3 g.). The crude material was chromatographed through a column of Sephadex G-25 (2.5×150 cm) and eluted with 1 M-aq. AcOH. The material which emerged in fractions 130 to 180 (fractions 99 drops each) was pooled and lyophilized to yield the title compound. $R_f$(BWA, 4:1:1) 0.45
Amino acid analysis: Asp (1) 0.90, Thr (2) 2.35, Ser (1) 1.10,
Phe (3) 3, Lys (1) 1.25, Cys and Trp N.D.
Antisecretory potency: at 4.40 mg/kg, total gastric volume and hydrogen ion secretion were significantly reduced.

Growth hormone, insulin and glucagon secretion were not inhibited at 1.90 mg/kg, the highest dose tested.

EXAMPLE VI

L-Alanyl-glycyl-L-cysteinyl-L-lysyl-L-asparaginyl-L-phenylalanyl-L-methionyl-L-tryptophyl-L-lysyl-L-threonyl-L-phenylalanyl-L-threonyl-L-seryl-L-cystein cyclic (3→14) disulfide The peptidoresin of example III (10 g.) was deprotected and oxidized to the cyclic disulfide form as described in example IV to afford crude material. This crude material was chromatographed through Sephadex G-25 and eluted with 50% aq. AcOH. The material which emerged in fractions 151 to 295 was pooled and lyophilized to afford impure material. This material was chromatographed again as above to afford (fractions 61-180) 3.5 g. of material. Further chromatography through Sephadex G-15 (800 mg. of the semi-purified material applied) and elution with 70% aq. AcOH gave the desired title peptide (fractions 63–89) 428 mg. $R_f$ (BWAP, 30:24:6:20) 0.66.

Amino acid analysis: Asp (1) 1.15, Thr (2) 2.29, Ser (1) 1.07, Gly (1) 1, Ala (1) 0.83, Cys (2) 1.35, Met (1) 0.84, Phe (2) 2, Lys (2) 2.11, NH$_3$ (1) 1.43, Trp N.D.

Antisecretory Potency: at 4.40 mg/kg, total gastric volume, pH and hydrogen ion secretion were significantly reduced.

Growth hormone, insulin and glucagon secretion were not inhibited at 1.0 mg/kg, the highest dose tested.

What is claimed is:

1. A compound selected from the group consisting of [des-Ala$^1$-Gly$^2$], Ala$^5$, Ser$^6$-somatostatin, Met$^7$-somatostatin, and [des-Ala$^1$-Gyl$^2$-Lys$^4$],-(3-mercapto-1-oxopropyl)$^3$-somatostatin, the reduced linear forms thereof and pharmaceutically acceptable salts thereof.

2. The compound of claim 1 which is [des-Ala$^1$-Gly$^2$], Ala$^5$, Ser$^6$-somatostatin.

3. The compound of claim 1 which is Met$^7$-somatostatin.

4. The compound of claim 1 which is [des-Ala$^1$-Gly$^2$-Lys$^4$], (3-mercapto-1-oxopropyl)$^3$-somatostatin.

5. A pharmaceutical composition for treatment of peptic ulcer disease comprising a gastric acid inhibiting amount of a polypeptide of the formulae:
   [des-Ala$^1$-Gly$^2$], Ala$^5$, Ser$^6$-somatostatin, Met$^7$-somatostatin, or
   [des-Ala$^1$-Gly$^2$-Lys$^4$], (3-mercapto-1-oxopropyl)$^3$-somatostatin, the linear reduced forms thereof or a non-toxic salt thereof
   and a pharmaceutically acceptable carrier.

6. A process for treating peptic ulcer disease which comprises administering to a mammal in need thereof a compound of the formulae
   [des-Ala$^1$-Gly$^2$], Ala$^5$, Ser$^6$-somatostatin, Met$^7$-somatostatin, or
   [des-Ala$^1$-Gly$^2$-Lys$^4$], (3-mercapto-1-oxopropyl)$^3$-somatostatin,
   the linear reduced forms thereof or a non-toxic salt thereof,
   in an amount sufficient to alleviate the symptoms of a peptic ulcer.

* * * * *